United States Patent [19]

Anraku et al.

[11] Patent Number: 4,856,533
[45] Date of Patent: Aug. 15, 1989

[54] VACUUM BLOOD-COLLECTION TUBE

[75] Inventors: Hideo Anraku, Ibaraki; Yoshikata Shoji, Shiga, both of Japan

[73] Assignee: Sekisui Kagaku Kogyo Kabushiki Kaisha, Osaka, Japan

[21] Appl. No.: 823,437

[22] Filed: Jan. 28, 1986

[30] Foreign Application Priority Data

Jan. 29, 1985 [JP] Japan ................... 60-15155
Jan. 29, 1985 [JP] Japan ................... 60-15156
Feb. 28, 1985 [JP] Japan ................... 60-39674

[51] Int. Cl.$^4$ ............................. A61B 5/00
[52] U.S. Cl. .................. 128/763; 604/403; 604/415
[58] Field of Search ............ 604/403, 415, 416, 82, 604/84, 86; 128/763, 764

[56] References Cited

U.S. PATENT DOCUMENTS

| 4,152,269 | 5/1979 | Babson . | |
| 4,153,739 | 5/1979 | Kessler . | |
| 4,212,307 | 7/1980 | Raitto | 128/763 |
| 4,236,120 | 3/1981 | Finley | 128/763 |
| 4,329,992 | 5/1982 | Becker et al. | 604/403 |
| 4,362,158 | 12/1982 | Lena | 604/415 |
| 4,397,318 | 8/1983 | Burns | 128/763 |
| 4,420,517 | 12/1983 | Ali | 604/403 |

FOREIGN PATENT DOCUMENTS 0106290 4/1984 European Pat. Off. .
2406988 5/1979 France .
2494985 6/1982 France .

Primary Examiner—C. Fred Rosenbaum
Assistant Examiner—Mark F. Colosimo
Attorney, Agent, or Firm—Armstrong, Nikaido, Marmelstein, Kubovcik & Murray

[57] ABSTRACT

A vacuum blood-collection tube comprising a tube-shaped vessel having an opening through which air can be removed, and a plug that makes the opening air-tight to maintain low-pressure conditions inside the said vessel, the raw materials of the said vessel being polyethyleneterephthalate, a copolymer of polyethyleneterephthalate, or an acrylonitrile resin, and the inner walls of said vessel incorporating a hydrophilic substance that is either difficult or impossible to dissolve in water and that prevent blood clots from adhering to the inner walls of said tube, a water-soluble substance, and a adsorptive inorganic substance.

11 Claims, 2 Drawing Sheets

VACUUM BLOOD-COLLECTION TUBE

BACKGROUND OF THE INVENTION

1. Field of the Invention

This invention relates to a container for use in blood test. More particularly, it relates to a vacuum blood-collection tube in which a whole sample of blood is collected from the person to be tested, and which is centrifugated to obtain the serum from the sample.

2. Description of the Prior Art

The rapid advances in techniques for clinical laboratory tests, along with the wider use of blood test, including serum biochemistry tests, serum immunological tests, corpuscle tests, and so on, are contributing to the prevention of disease and also to diagnosis at early stages. The majority of blood tests are serum tests, and usually the serum that is required for such tests is collected as blood in a container for use in blood tests, and allowed to coagulate; the serum is then collected by centrifugation, by which the blood clot (a mass made of a gel mixture of fibrin and blood corpuscles) is separated.

Syringes are used to collect blood from the person to be tested, but recently, a blood-sampling method in which vacuum blood-collection tubes are used is also available. When vacuum blood-collection tubes are used to collect blood, the blood is collected into the vacuum blood-collection tube by the introduction of vacuum conditions through a special blood-collection tube holder.

The raw materials used for vacuum blood-collection tubes are either synthetic resins such as polymethylmethacrylate, etc., or glass. However, in vacuum blood-collection tubes made of these raw materials, when the blood is collected, quite a long time is required for the blood to coagulate so that the serum and the blood clot can be separated, and the serum that is required for the test can not necessarily be available rapidly. This becomes a particular problem when the test is an emergency one. Even in vacuum blood-collection tubes made of glass, in which blood coagulation time is shorter, from 40 to 60 minutes are required after the blood is collected until coagulation has taken place. When vacuum blood-collection tubes made of synthetic resins are used, it is necessary to allow the tube to stand for four hours or more, in practice. Also, in vacuum blood-collection tubes made of synthetic resins or glass, the fibrin and the blood clot in the form of a gel readily adhere to the side of the tube in solidified form, which reduces the sample volume of the serum. In addition, fibrin readily remains in the serum, and for that reason, causes a problem by interfering with serum biochemistry test results. When vacuum blood-collection tubes made of glass, which gives relatively a good separation of the serum, are used, the separation becomes extremely poor when the temperature is 15° C. or below, so that the separation is poor in the low-temperature conditions of winter.

When extremely fine grains of an inorganic substance such as glass, etc., are attached to the walls of the tube, the coagulation time of the blood is shortened. When a separating agent incorporating silicon oil, powdered silicon compounds, etc., is present in the blood-collection tube, this causes an increase in the separability of the serum. Such separating agents use the property of thixotropy, and are prepared so as to have a specific gravity of the intermediate between that of the serum and the blood clot. For that reason, after the blood that has been collected is allowed to coagulate, and when the blood-collection tube is placed in a centrifugal field, the separating agent moves to the interface between the serum layer and the clotted blood layer, separating them. If it will take time until the various kinds of tests will take place on the sample serum prepared by the above-mentioned process, the blood-collection tube is stored as it is at a temperature of less than 4° C. However, the possible storage time is relatively short, being about 48 hours in the case of blood-collection tubes made of glass; even in blood-collection tubes made of polymethylmethacrylate, the time is as short as about 72 hours.

If vacuum blood-collection tubes are stored having internal low pressure before blood is collected, then, because the collection tube has some permeability to gas, the low-pressure conditions inside the tube are rapidly lost, due to atmosphere oxygen, carbon dioxide, water vapor, etc.

To solve the above-mentioned problems, vacuum blood-collection tubes are ordinarily vacuum-wrapped in a separate wrapping material. The wrapping material used for the vacuum-wrapping is, for example, a metal can, or a laminated film of aluminum foil, etc. Metal cans are rigid, so they are excellent in the protection of vacuum blood-collection tubes. In addition, they act as excellent gas barriers. Their defects are that they are heavy and bulky. They are also expensive. Laminated films of aluminum foil are flexible, and have the advantages of not being hard or bulky. However, in making the vacuum blood-collection tube air-tight, there is the possibility of injuring them by crushing. The resistance and the strength against being ripped of aluminum foil are inferior, and pinholes readily form when, for instance, a section of the foil is crumpled. Once a gas such as oxygen has been allowed into the inside of the wrapping material of aluminum foil, the low-pressure conditions inside the vacuum blood-collection tube are lost. Accordingly, the ability of aluminum foil to act as a gas barrier is imperfect.

SUMMARY OF THE INVENTION

The vacuum blood-collection tube of this invention which overcomes the above-discussed and numerous other disadvantages and deficiencies of the prior art, comprises a tube-shaped vessel having an opening through which air can be removed, and a plug that makes the opening air-tight to maintain low-pressure conditions inside the said vessel, the raw materials of the said vessel being polyethyleneterephthalate, a copolymer of polyethyleneterephthalate, or an acrylonitrile resin, and the inner walls of said vessel incorporating a hydrophilic substance that is either difficult or impossible to dissolve in water and that prevent blood clots from adhering to the inner walls of said tube, a water-soluble substance, and a adsorptive inorganic substance.

The adsorptive inorganic substance has, in a preferred embodiment, an absorption amount of linseed oil of 20–40 ml/100 g and a BET-specific surface area of 5,000–30,000 cm$^2$/g.

A partitioning agent is, in a preferred embodiment, used within said vessel. The partitioning agent contains, in a preferred embodiment, both agents that confer the property of thixotropy and viscous liquid. Alternatively, the partitioning agent contains, in a preferred embodiment, thixotropy-conferring agents, viscous liquids and water-insoluble amines.

The tube-shaped vessel is, in a preferred embodiment, wrapped so as to be air-tight in a plastic wrapping that acts as a gas barrier, the space between said tube-shaped vessel and said wrapping being filled with a gas that does not readily permeate either the vessel material or the wrapping material, and the pressure of said gas being greater than atmospheric pressure. The amount of said gas that permeates both the tube-shaped vessel and the wrapping is, in a preferred embodiment, 2 cc/m$^{2\cdot24}$ hrs atm or less at 23° C. The wrapping is, in a preferred embodiment, made of a laminate.

Thus, the invention described herein makes possible the objects of (1) providing a vacuum blood-collection tube in which a whole blood sample that has been collected can coagulate in a short period of time, and which is placed in a centrifugal field resulting in an effective separation of the serum and the blood clot; (2) providing a vacuum blood-collection tube in which after centrifugation, the tube can be stored as it is for a long time at low temperatures without decrease in the quality of the serum; that is, providing a vacuum blood-collection tube that also acts as a storage vessel for blood serum; (3) providing a vacuum blood-collection tube in which the space between the tube-shaped vessel and the wrapping material is filled with a gas of low permeability at a pressure greater than atmospheric pressure, so that the low-pressure conditions inside the tube-shaped vessel can be maintained with certainty for long periods of time; (4) providing a vacuum blood-collection tube wrapped in a wrapping made of a material that is markedly better than the material used conventionally for wrapping vacuum blood-collection tubes in its ability to act as a gas barrier; and (5) providing a vacuum blood-collection tube wrapped without damage in a wrapping material that has excellent flexibility, is light, is not bulky, and is low in cost.

BRIEF DESCRIPTION OF THE DRAWINGS

This invention may be better understood and its numerous objects and advantages will become apparent to those skilled in the art by reference to the accompanying drawings as follows.

DESCRIPTION OF THE PREFERRED EMBODIMENTS

Figure 1:
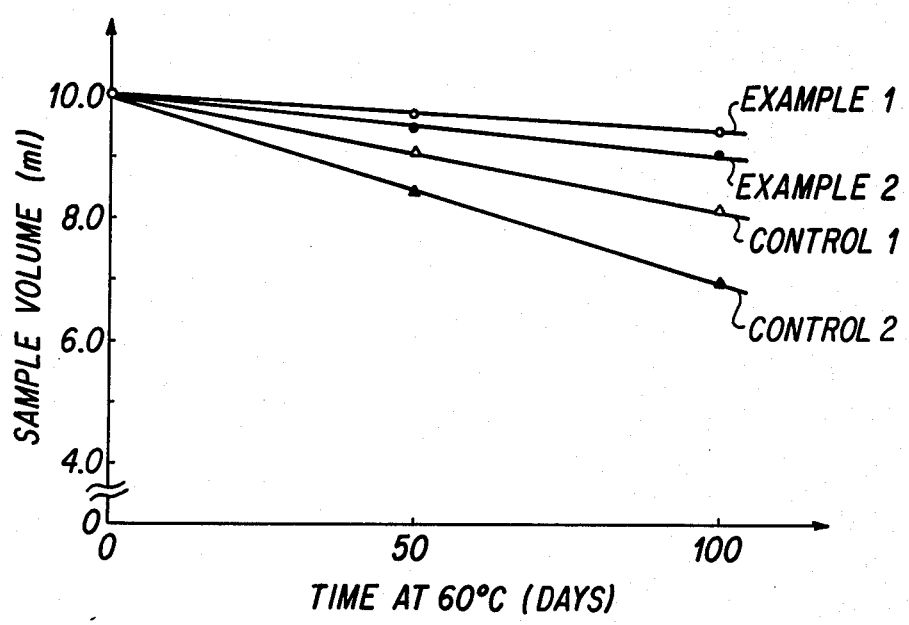
FIG. 1 is a graph of the experimental data shown in Table 3.

The raw materials of a tubular vessel forming a vacuum blood-collection tube of the present invention are, for example, the polyethylene terephthalate of the structural formula shown below:

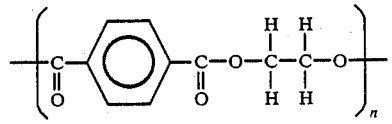

Polyethyleneterephthalate is highly crystalline, so that to control this property, a copolymer of polyethyleneterephthalate copolymerized with an agent to control crystallization such as 1,4-cyclohexanedimethanol, etc., at the proportion of 1-50% by weight can be used. Polyethyleneterephthalate has an excellent ability to act as a gas barrier, and when it is used for the vacuum blood-collection tubes of the present invention, it makes it possible to maintain low pressure at a fixed level. In addition, its resistance to impact is better than that of glass or of polymethylmethacrylate, and no damage arises from low pressures. Disposal after use can be destruction by fire, which is not possible in the case of vacuum blood-collection tubes that are made of glass.

Also, acrylonitrile resins may be used as raw materials for the tube-shaped vessel of the vacuum blood-collection tubes of this invention. For the acrylonitrile resins that may be used in the present invention, a resin, the main ingredient of which is polymerized acrylonitrile, is indicated, and generally, a copolymer of acrylonitrile and a small amount of butadiene, etc., as the rubber ingredient, and/or one kind or two or more kinds of acrylates and/or methacrylates such as methyl acrylate, methyl methacrylate or the like are used.

Such acrylonitrile resins have excellent abilities to act as a gas barrier, so that when they are used in the vacuum blood-collection tubes of the present invention, it is possible to maintain a fixed level of reduced pressure. Also, their resistance to shock is much better than that of glass or polymethylmethacrylate, and there is no danger of damage arising from the process of bringing about low pressure. For disposal after use, it is possible to destroy the tubes by fire, which cannot be done with vacuum blood-collection tubes made of glass.

For the air-tight plug of the opening of vacuum blood-collection tubes in which low-pressure conditions are to be maintained, it is desirable to use articles constructed from raw materials known to those skilled in the art such as isobutylene-isoprene rubber or chlorinated isobutylene-isoprene rubber.

To keep the inside of the blood-collection tube at low pressure, the above-mentioned rubber stopper should be applied to the said tube within a container at a low pressure.

In the vessel for use in blood tests of the present invention, the surface of the inner walls should contain a hydrophilic substance that is difficult or impossible to dissolve in water and that prevents the blood clot from adhering to the inner walls of the tube, a water-soluble substance, and an absorptive inorganic substance.

For the hydrophilic substance that is difficult or impossible to dissolve in water and that prevents the blood clot from adhering to the inner walls of the tube, examples thereof are modified aliphatic silicone oils, modified aromatic silicone oils, modified paraffin, modified wax, etc. Examples of the modified aliphatic silicone oils are dimethylpolysiloxane, methylhydrogenpolysiloxane, etc., into which polar groups have been introduced. Examples of the polar groups are hydroxyl groups, amino groups, carboxyl groups, epoxy groups, polyether groups, etc. An example of the modified aromatic silicone oils is methylphenylpolysiloxane, etc., into which the above-mentioned polar groups have been introduced. The modified paraffin and the modified wax are paraffin and wax into which the above-mentioned polar groups have been introduced. Partially esterified polyhydric alcohols, partially esterified polyglycols, etc., can be used. The most preferable example thereof is silicone oil into which polar groups have been introduced. The above-mentioned hydrophilic substances are not surface-active agents, but when they are present on the inside wall of the vessel, they prevent the blood clot from sticking to the surface of the inner wall, and if the blood clot should become attached, they act to peel the clot from the surface.

As the water-soluble substance, it is possible to use either water-soluble compounds of low molecular weight, or those of high molecular weight. The water-soluble compounds of low molecular weight are, for example, ethyleneglycol, glycerin, sorbitol, etc. Those of high molecular weight are, for example, polyethyleneoxide, polyvinylalcohol, polyvinylpyrrolidone, sodium polyacrylate, polyethyleneimine, sodium alginate, starch, pullulan, methylcellulose, hydroxyethylcellulose, hydroxypropylcellulose, carboxymethylcellulose, cellulose acetate phthalate, gum arabic, tragacanth gum, locust bean gum, guar gum, pectin, carrageenan, furcellaran, glue, gelatin, casein, etc. The most preferable examples are polyvinylpyrrolidone, polyethylene oxide, etc. These water-soluble substances prevent the above-mentioned hydrophilic substance from covering the surfaces of the inorganic adsorptive substances, thereby preventing a decrease in the acceleration of blood coagulation caused by these adsorptive inorganic substances. These water-soluble substances act to improve the contact between the adsorptive inorganic substances and the blood.

The adsorptive inorganic substances are water-insoluble inorganic fine-grain substances that are used as adsorptive agents, such as glass, silica, kaolin, cerite, benthonite, etc.

The diameters of the particles of the adsorptive inorganic substance should be 50 $\mu$m or less, and it is preferable for the mean diameter to be 10 $\mu$m or less. A particularly effective adsorptive inorganic substance for shortening the coagulation time of blood is silica, especially porous silica containing amorphous substance present at 20% by weight or more, which gives excellent results.

Such adsorptive inorganic substances accelerate the activity of blood coagulation factors when touching the blood, and moreover act to stimulate the agglomeration of platelets. However, in order that the adsorptive inorganic substance effectively causes the acceleration of blood coagulation, it is desirable to keep the absorption amount of linseed oil, BET-specific surface area, and the specific resistance within fixed limits.

The absorption amount of linseed oil and the BET-specific surface area express the extent of the surface area of the adsorptive inorganic substance, and the surface area is correlated with the extent of spaces between the pores on the surface of the adsorptive inorganic substance. Thus, depending on the absorption amount of oil and the BET-specific surface area, it is possible to know the extent of spaces between the pores on the surface thereof. As the desirable adsorptive inorganic substance for this invention, the absorption amount of linseed oil should be 20-40 ml/100 g, and the BET-specific surface area should be 5000-30,000 cm$^2$/g.

The absorption amount of linseed oil follows that established in JIS K-5101. The BET-specific surface area is a value which is calculated as follows: The amount of gas to cover the surface completely as a layer of single molecules is, first, obtained from the amount of gas adsorbed onto the surface of the adsorptive inorganic substance, the equilibrium pressure at that time, and the vapor saturation pressure of the adsorbing gas. The result is then multiplied by the mean sectional area of the adsorptive gas molecules, resulting in a value for the BET-specific surface area. The adsorptive gas may be nitrogen gas, oxygen gas, argon gas, methane gas, etc. Thus, by this method, it is possible to calculate the surface area including the pores, which cannot be directly calculated by the measurement of the adsorption amount of linseed oil.

At the time of blood coagulation, activation of the XII factor (i.e., the contact factor) is attained. For that, it is necessary that three substances, prekallikrein, a kininogen of high molecular weight, and the XII factor form a complex on the surface of a foreign substance and that the complex is adsorbed therein. If one or two of these substances are lacking, the activation of the XII factor will not take place. When adsorptive inorganic substances are used in the expectation that they will act to accelerate the coagulation of the blood, if the surface area is extremely large, a complex is not formed on the surface of the absorptive inorganic substance, and the proportion adsorbed of the XII factor, the prekallikrein, and the kininogen of high molecular weight is increased. In other words, the percentage of complex formation of the three substances required for the activation of the XII factor decreases. Accordingly, this means that, on the contrary, the effect of accelerating the blood coagulation decreases. In reverse, if the surface area of the adsorptive inorganic substance is too small, the probability of adsorption of the coagulation factor becomes less, and an effect of acceleration of blood coagulation cannot be expected. For that reason, the preferred limits of the conditions for the adsorptive inorganic substance for this invention are an absorption amount of linseed oil of 20-40 ml/100 g, and a BET-specific surface area of 5,000-30,000 cm$^2$/g.

The specific resistance of the adsorptive inorganic substance of the present invention is preferably $1 \times 10^{10} \Omega \cdot$cm or less, more preferably $5 \times 10^{4} \Omega \cdot$cm or less. At ordinary temperatures, the specific resistance is the reciprocal of electrical conductivity. With an adsorptive inorganic substance, the specific resistance maintains the adjustability of the distribution of electrical potential between the protein and the adsorptive inorganic substance, and contributes to preventing changes in the conformation of the protein.

Adsorptive inorganic substances act to accelerate the coagulation of blood, but on the other hand, such adsorptive inorganic substances make adhesion to the wall surface of the vessel by the blood clot more likely, so that even when the coagulated blood is put into a centrifuge, the separation of serum and blood clot into phases may be difficult. However, the above-mentioned hydrophilic substances and water-soluble substances, when present, improve the tendency of the blood clot to adhere, which is caused by the adsorptive inorganic substance, without damaging the effect of acceleration of blood coagulation.

That various substances mentioned above are in the inner wall of the vessel means that nowhere else but the wall, either the inner wall of the vessel or the inner part of the wall contain these substances. For example, each of the above-mentioned substances, the hydrophilic substance, the water-soluble substance, and the adsorptive inorganic substance, are either dissolved or dispersed in a suitable solvent and/or a suitable binder, and the resultant mixture is sprayed onto the surface of the inner wall of the vessel, or the inner surface is soaked in this mixture. Alternatively, the above-mentioned hydrophilic substance is mixed into the polyethyleneterephtalate pellet or acrylonitrile resins and a vessel is made of the mixture; then a mixture of the water-soluble substance and the adsorptive inorganic substance in a suitable solvent and/or a suitable binder is applied to the inner wall of the vessel by a spray or soaking treatment.

The amount of the above-mentioned hydrophilic substance and water-soluble substance that should be present on the inner wall of the vessel is preferably $1 \times 10^{-10}$ g/cm$^2$ or more. The amount of the adsorptive inorganic substance that should be present is preferably $1 \times 10^{-6}$ g/cm or more. If there is an excessive amount, this will interfere with the results of the blood tests. Therefore, there should be no more than $1 \times 10^{-2}$ g/cm$^2$ of all of these substances taken together.

Thus, according to the present invention, blood coagulation factors are rapidly activated, and the time required for the blood to coagulate is much shortened. Moreover, fibrin, which causes blood coagulation, and the resultant blood clot do not adhere to the inner wall of the vessel, so that separation of serum and the blood clot is satisfactory, and there is no problem arising from there being fibrin or parts of the blood clot mixed into the serum that is obtained after separation. Moreover, since the components of the blood clot are contracted enough, a larger yield of serum is obtained.

Generally, biochemistry tests in which only serum can be used are numerous. After centrifugation, the serum that is obtained is sucked up into a pipette from the vessel for use in blood tests. However, this step of sampling takes time. Transporting the vessel as it is not advisable. For that reason it is normal to supply an agent that forms a partition inside the vessel. As the agent has a composition that has thixotropy and that forms a partition at the position between the serum and blood clot after centrifugation, it is possible to decant the serum. Substances that are thixotropic preferably include inorganic fine powder such as silica, alumina, glass, talc, kaolin, benthonite, titania, zirconium, asbestos, carbon black, etc., organic fine powder such as styrene polymers and copolymers, acrylic resins and polyvinyl chloride Of these agents that confer the property of thixotropy, a fine silica powder gives the best results. This fine silica powder contains a fine powder in which the main component is anhydrous silicic acid. The fine powder is, as desired, treated for hydrophobicity by a graft reaction or a coupling reaction. It is possible to use the starting material in the natural state as a powder or as a mass. It is desirable for the mean diameter of these agents that confer the property of thixotropy to be 1 m$\mu$ to 100 $\mu$. It is difficult to handle the agent if the diameter is less than 1 m$\mu$, and also, as mentioned below, when it is mixed with a viscous liquid and agglomeration takes place, secondary particles form, and it is difficult to obtain uniform dispersion. If the diameter is more than 100 $\mu$, the stability of the dispersion in the viscous liquid is inferior, and the partitioning agent as a whole lacks uniformity of flow. In addition, with a specific surface area of 10-500 m$^2$/g, the thixotropy that occurs is excellent. However, if the specific surface area is less than 10 m$^2$/g, it is difficult for the inorganic fine particles to become compatible with the viscous liquid which is a component of the composition used for separation, and the particles readily sediment out under such circumstances. When the specific surface area is larger than 500 m$^2$/g, agglomeration occurs readily, and it is difficult to achieve uniform dispersion in the viscous liquid.

For the viscous liquid, it is acceptable to use either one that has strong mutual effects with the agent that confers thixotropy, or one that does not have strong mutual effects. Also, it is advisable to use substances that are compatible with each other.

To have strong mutual effects with the agent that confers thixotropy means that after uniform dispersal of the mixture of a certain agent that confers the property of thixotropy with a certain viscous liquid, and even after 30 minutes of centrifugation at 4000 rpm in a separation centrifuge with an arm length of 10 cm, layers of the components of the above-mentioned mixture cannot be seen.

The reason for such mutual effects is not known, but possibly hydrogen bondings that arise between materials having hydrophilic groups are the main cause, and perhaps aggregation arising between materials without hydrophilic groups because of their molecular structures is a cause.

As viscous liquids that have a strong mutual effect with agents that confer the property of thixotropy, the animal and plant oil, and the said oils and liquid polymers into which acid radical (e.g., maleic acid) have been introduced can be used. The animal and plant oils are, for example, soybean oil, linseed oil, safflower oil, fish oil, etc. The liquid polymers are, for example, acryl resin oligomers, polyester oligomers, liquid polyisoprene, liquid polybutene, liquid polybutadiene, etc. Also, the animal and plant oils and liquid polymers into which epoxy groups have been introduced can be used. When the agents that confer the property of thixotropy are organic powders, as the viscous liquid the same kind of oligomer as the thixotropy-conferring agents can be used. For instance, when the agent is styrene, styrene oligomer can be used as the viscous liquid. Whichever is used, a viscosity of 200 cps or more is desirable. When such viscous liquids are used, separation of the thixotropy-conferring agent from the viscous liquid as causing problems does not occur.

Even viscous liquids that do not have a strong mutual effect with agents that confer the property of thixotropy can be used in the presence of water-insoluble amine compounds in connection with the present invention. As such a viscous liquid, other liquid substances of high molecular weight such as liquid paraffin, liquid polyisoprene, liquid polybutene, liquid polybutadiene, etc., and styrene oligomers and their chlorinated compounds can all be used. When the thixotropic agent is a resin of the styrene type, liquid paraffin and its chlorinated compounds can be used, the viscosity of which is preferably 1000 cps or more.

It is also possible to use a mixture of a viscous liquid that has a strong mutual effect with a thixotropic agent and another viscous liquid that does not have a strong mutual effect with the thixotropic agent but is readily compatible with that viscous liquid. In this case, the phrase "readily compatible" is used to describe the situation in which after the two viscous liquids are mixed until dispersion is uniform, and after this mixture is left for one week at ordinary temperatures, there is no phase separation.

When the mixture of a viscous liquid that has a strong mutual effect with a thixotropic agent and another viscous liquid that does not have a strong mutual effect with the thixotropic agent but is readily compatible with that viscous liquid is used, its viscosity is stable for a long period. In such a case, suitable limits should be established for the relative proportions of the two viscous liquids in the mixture with careful consideration given to the strength of the mutual action with the thixotropic agent. Ordinarily, with a viscous liquid having a strong mutual effect with a thixotropic agent, for 100 parts by weight of the liquid, 10-600 parts by weight of the viscous liquid that does not have strong mutual effects with the thixotropic agent can be used.

Such stability of the viscosity of the mixture becomes yet greater when water-insoluble amine compounds are used. For the water-insoluble amine compounds, compounds with one or more alkyl groups containing eight or more carbon atoms are desirable, examples of which are dodecylamine, tetradecylamine, hexadecylamine, octadecylamine, dodecyldimethylamine, tetradecyldimethylamine, octadecyldimethylamine, polyoxyethyleneoctadecylamine, trioctylamine, etc.

The reason why the above-mentioned amine compounds are used is that they have the property of being readily adsorbed onto the surface of the thixotropic agent and that they have mutual effects with both the thixotropy-conferring agent and the viscous liquid so that the stability of the degree of viscosity can be increased even as time lapses. The reason for amines with alkyl groups having eight or more carbon atoms being desirable is not only that these amines are superior in having a high degree of insolubility in water and in the property of not dissolving into the separated serum or blood clot, but also that long-chain alkyl groups of the amine compounds that are adsorbed onto the surface of a thixotropic agent act together to increase the stability.

By the use of the above-mentioned amine compounds, the stability of the degree of viscosity of the partitioning agent is markedly improved, and as a result, separation is done using a centrifuge, and the partition is very stable.

Concerning the proportions of the thixotropy-conferring agent and the viscous liquid that should be used, for 100 parts by weight of the viscous liquid, 2-15 parts by weight of the thixotropic agent is used, and when water-insoluble amine compounds are used, using 0.02-5 parts by weight thereof is preferable.

The specific gravity of the partitioning agent is ordinarily 1.03-1.08 at ordinary temperatures, because in order to form a partition between the serum and the blood clot, the partitioning agent must have a specific gravity between the specific gravity of the serum and that of the blood clot.

When such a partitioning agent is used, the serum and the blood clot are separated by centrifugation, and a partition is formed at the interface between the serum and the blood clot. Once the partition is formed, it is stably maintained and will not be destroyed even though the vessel is tilted to one side, so that the serum can readily be obtained by a simple procedure such as decantation.

To obtain the vacuum blood-collection tube of the present invention, it is necessary first to form a tube-shaped vessel by the appropriate molding procedures of injection molding, blow molding, compression molding, transfer molding, vacuum molding, casting molding, etc., using polyethyleneterephthalate, polyethyleneterephthalate copolymers, or acrylonitrile resins. At that time, as mentioned above, it is acceptable to mix a hydrophilic substance therein. Alternatively, on the inner surface of the wall of the vessel made in this molding technique, the above-mentioned method is used to incorporate a hydrophilic substance, a water-soluble substance, and an adsorptive inorganic substance. This tube should then be sealed with a seal that makes the vessel air-tight. In addition, the partitioning agent may be placed, in advance, in the tube, or it may be added after the sampled blood is allowed to coagulate, during the step of centrifugation.

The vacuum tube with the inner section of which made in this way and brought to have low pressure is used to collect blood from the person to be tested, and the blood is left at ordinary temperatures for about 20-30 minutes to coagulate. Then the tube is placed in a centrifuge and the serum and blood clot are separated by centrifugal force.

The raw material of the vessel of the vacuum blood-collection tube of this invention is either polyethyleneterephthalate, a copolymer of polyethyleneterephthalate, or acrylonitrile resin, which has low hydrophilicity, and thus unlike with conventional hydrophilic materials, such as, for example, glass or polymethylmethacrylate, there is no layer of water molecules adsorbed on the inner surface of the vessel where it touches the blood. For that reason, there is strong adherence of the partitioning agent and the inner surface of the wall of the collection vessel, so that the separation of serum and the blood clot can be complete. For that reason, it is assumed by the inventors that inorganic ions from the blood clot do not pass through a layer of water molecules on the inner surface of the wall to reach the layer of serum. Therefore, the serum obtained by separation in a centrifuge can be stored for long periods of time at low temperatures. When the vacuum blood-collection tube of the present invention is used, it is possible to store the serum at 4° C. for 340 hours or more. This is about seven-fold the time for which collection tubes made of glass can be stored with sample. When a conventional vacuum blood-collection tube containing a partitioning agent is used, a layer of water molecules forms on the inner surface as an adsorbed layer, and the partitioning agent does not firmly adhere to the side of the collection tube, so that the isolation effect is not attained, and inorganic ions, etc., from the blood clot diffuse to the serum layer. The result is that centrifuged serum cannot be stored for long periods of time.

As mentioned above, when the vacuum blood-collection tube of the present invention, made of specific raw materials, is used, the whole-blood sample that is collected coagulates in a short time, and the serum and the blood clot are effectively separated by the step of centrifugation. Moreover, after centrifugation as well, the serum can be stored in the same collection tube, so that the collection tube may also be used as a storage tube.

In order that the oxygen, carbon dioxide, water vapor, etc., in the atmosphere are completely shut out, and that the low pressure inside of the tube can be maintained for long periods of time, the above-mentioned vacuum blood-collection tube is preferably wrapped in a plastic wrapping.

As a wrapping technique by which a container to be wrapped is prevented from touching the outer parts thereof, there is a vacuum-wrapping method in which the space between the inner wrapping and the outer wrapping is a vacuum. There is also a gas-filled wrapping method in which the space therebetween is filled with a gas. The method of gas-filled wrapping is used to prevent the acidification of food products, to prevent the growth of molds and bacteria, to prevent oxidation of electrical parts, welding rods, and other metal materials, and to prevent rusting. There are a great many gases that can be used for the filling, but ordinarily, nitrogen or carbon dioxide are used separately or in a mixture with a specific ratio of the two.

This invention was completed based on knowledge of the inventors that the above-mentioned vacuum blood-collection tube is wrapped in a plastic wrapping and the space therebetween is filled with a gas that does not permeate either of these materials and that is at a pressure greater than atmospheric pressure, and thus the low-pressure conditions inside the vacuum tube can be maintained for a long period of time.

According to the present invention, the vacuum blood-collection tube is wrapped in a plastic wrapping material, and the space between the tube-shaped vacuum blood-collection tube and the plastic wrapping material is filled with a gas, which does not readily permeate either the tube or the plastic wrapping. The pressure of the gas is established at greater than atmospheric pressure. Thus, the problems with the ability of a plastic wrapping to act as a gas barrier are solved. This solution is based on the use of the following principles of reverse osmosis: "By use of a pressure greater than osmotic pressure through a semipermeable membrane, it is possible to suppress the movement of chemical species through that membrane." Therefore, when the inside of the plastic wrapping is filled with a gas, this prevents the permeation of gases in the atmosphere, such as oxygen, carbon dioxide, water vapor, etc., into the inside of the wrapping. Thus, the plastic vessel shaped like a tube, made of polyethyleneterephthalate, a copolymer of polyethyleneterephthalate, an acrylonitrile resin, etc., is not touched by such gases, and the low pressure existing inside the tube can be maintained for long periods of time. Because the gas used for filling also has the function of protecting the tube-shaped vessel, this vessel is not damaged by shock to the outside of the wrapping.

For the above-mentioned plastic wrapping material, all known plastics can be used. A preferable plastic wrapping is, for example, a laminate of a film composed of at least one of ethylene-vinylalcohol copolymer, polyacrylonitrile, polyvinylidenechloride, polyvinylchloride, plyethyleneterephthalate, nylon, etc., another film composed of at least one of polyethylene, polypropylene, etc. This provides for a light, non-bulky, and inexpensive packing material. It is also possible to use aluminum foil covered with polyethylene or polyester.

As the gas to be used for filling the space, any gas that has a vapor pressure at ordinary temperatures that is greater than atmospheric pressure can be selected. For example, hydrocarbon derivatives of one to four carbon atoms, in which fluorines, chlorines or bromines are substituted for hydrogen atoms; alcohols of one to four carbon atoms in which fluorines, chlorines, or bromines are substituted for hydrogen atoms; ethers of one to four carbon atoms in which fluorines, chlorines, or bromines are substituted for hydrogen atoms; alkanes of one to four carbon atoms in which fluorines, chlorines, or bromines are substituted for hydrogen atoms; inert gases such as nitrogen, argon, and xenon, etc., can be used. Of the above, nitrogen and freon gas are most preferable for use. Of these gases, the gas to be used depends on the raw materials used in the construction of the tube-shaped vessel of the vacuum blood-collection tube and of the wrapping materials, and an appropriate choice is of a gas that does not readily permeate either of the two. By "not readily permeating" is meant a gas permeation value of 2 cc/m²·24 hrs. atm or less at 23° C. for both the tube-shaped vessel and for the wrapping. This value for gas permeation is according to that established by the ASTM D 1434.

EXAMPLE 1

Carbinol-modified silicone oil, which was prepared by the introduction of hydroxyl groups into polydimethylsiloxane, as the hydrophilic substance; polyvinylpyrrolidone as the water-soluble substance; and finely powdered silica (with a mean diameter of 4 μm, the absorption amount of linseed oil of 30 ml/100 g, a BET-specific surface area of 12,000 cm²/g, and a specific resistance of $2,6 \times 10^{44} \Omega \cdot cm$) as the adsorptive inorganic substance, were used. The hydrophilic substance, the water-soluble substance, and the adsorptive inorganic substance were dispersed into methyl alcohol with concentration of 0.1 weight %, 0.1 weight %, and 1.0 weight %, respectively.

Two kinds of tube-shaped vessels with a capacity of 10 ml were prepared, one of which was made of polyethyleneterephthalate, and the other of which was made of polyacrylonitrile resin (trade name, BAREX 210; sold by Mitsuitoatsu Kagaku Co., Ltd., Japan) which is a copolymer of acrylonitrile, a small amount of butadiene, and a small amount of acrylic ester.

On each inner surface of these tube-shaped vessels, the above-mentioned dispersion liquid was sprayed, and after air-drying, the inner gas thereof was removed and the vessels were sealed with a butyl rubber stopper, resulting in two kinds of vacuum blood-collection tubes. The pressure within both of these kinds is set so as to obtain a blood sample volume of 6 ml.

Each vacuum blood-collection tube obtained is used to sample human fresh blood, and each is left at 20° C. The time required for the whole blood to lose its ability to flow, that is, the blood coagulation time, is measured, and evaluated as an index of the coagulability of the blood.

After coagulation of the blood, each vacuum blood-collection tube is centrifuged at 3000 rpm for 5 minutes, to bring about centrifugal separation, after which the state of separation of the serum is observed. Example 1 in Table 1 indicates that the blood coagulation in each vacuum blood-collection tube was extremely rapid, and that the separation of the serum was good.

EXAMPLE 2

Seventy parts by weight of chlorinated polybutene with a specific gravity of 1.02 at 20° C. and a viscosity of 10,000 cps, 21 parts by weight of epoxidized soybean oil with a specific density of 1.0 at 20° C. and a viscosity of 1700 cps, 9 parts by weight of silica gel that has been treated so as to become hydrophobic, and that is finely powdered, and 0.2 parts by weight of trioctylamine were kneaded in a three-roller kneading machine, giving a partitioning agent with the specific density of 1.06 at 20° C.

One gram of this partitioning agent is placed into each of the two kinds of blood-collection tubes obtained by the methods of Example 1 the tubes are given a low pressure in their inner part sufficient for the sampling of 6 ml of blood, and each is sealed with a butyl rubber stopper so as to be air-tight.

Using the resultant vacuum blood-collection tube and sample, the coagulability of the blood and the condition of the separation of the serum are observed in the same manner as in Example 1. The results for the two different kinds of vacuum blood-collection tubes are shown in Table 1 in the column for Example 2. As is clearly shown there, the coagulation of the blood sample sampled using these collection tubes is rapid, and the separation of the serum is good.

To observe the ability of such vessels to act as storage vessels for serum, each vacuum blood-collection tube was stored in a refrigerator at 4° C., and the values of the results of the biochemical tests for LDH and K were measured using serum immediately after being stored and, also serum stored for 3 days, for 7 days, and for 14 days. The results are given in Table 2 in the column for Example 2. The results clearly show that LDH and K both gave stable values, so that these vessels are suitable for the storage of serum.

Control 1

Two vacuum blood-collection tubes made of glass with a capacity of 6 ml for the blood sample were used, said tubes being commercially available ones. Using these, the blood coagulation time and the condition of serum separation were observed under the same conditions as in Example 1. Also, both tubes were stored under the same conditions as used in Example 2, in order to examine the suitability of these tubes for storage of serum. The results are shown in the control column of Tables 1 and 2.

TABLE 1

| | Blood Coagulation Time | Serum Separation |
|---|---|---|
| Example 1 Polyethyleneterephthalate tube-shaped vessel | 30 min. | Very good |
| Acrylonitrile resin tube-shaped vessel | 25 min. | Very good |
| Example 2 Polyethyleneterephthalate tube-shaped vessel | 25 min. | Very good |
| Acrylonitrile resin tube-shaped vessel | 25 min. | Very good |
| Control 1 | 60 min. | Fibrin sediment |
| | 50 min. | Fibrin sediment |

TABLE 2

| | | immediately after | Day 3 | Day 7 | Day 14 |
|---|---|---|---|---|---|
| Example 2 | Polyethyleneterephthalate tube-shaped vessel LDH (w · unit) | 210 | 214 | 205 | 215 |
| | K (m Eq/l) | 5.1 | 5.1 | 5.2 | 5.1 |
| | Acrylonitrile resin LDH (w · unit) | 180 | 187 | 183 | 185 |
| | tube-shaped vessel K (m Eq/l) | 4.9 | 4.9 | 5.0 | 4.8 |
| Control 1 | LDH (w · unit) | 208 | 220 | 280 | 342 |
| | K (m Eq/l) | 5.1 | 6.1 | 13.0 | 15.9 |
| | LDH (w · unit) | 179 | 191 | 225 | 283 |
| | K (m Eq/l) | 5.0 | 6.1 | 10.5 | 15.2 |

EXAMPLE 3

Vacuum blood-collection tubes made of polyethyleneterephthalate in the same manner as in Example 1 and with a sample capacity of 10 ml were wrapped in a laminated film that could act as a gas barrier, and the inside of the package was filled with gas. Laminated film that could act as a gas barrier, was a layered material that consisted of, from the outside, drawn polypropylene 20 μm thick, an ethylene-vinylalcohol copolymer (trade name, EVAL, CRARE Co.) 17 μm thick, and polyethylene, 55 μm thick. The gas used for filling was pentafluoromonochloroethane, and the pressure after filling was 1.2 atmospheres. The wrapped tube and packing were placed in an oven heated to 60° C. After either 50 or 100 days of being heated, the tubes were removed from the oven and used to sample blood. Variations in the amount of blood sampled were looked for. The results are, shown in Table 3. As is clearly shown there, even when the vacuum blood-collection tubes were stored at a high temperature for a long period of time, the extent of the vacuum and the amount of blood sampled were very well maintained.

EXAMPLE 4

Variations in the amount of blood sampled in vacuum blood-collection tubes were looked for under the same conditions as in Example 3, except that nitrogen gas was used for the filling gas. The results are shown in Table 3. As in Example 3, the extent of the vacuum and the amount of blood sampled were very well maintained.

CONTROL 2

The same vacuum blood-collection tubes and laminated film with the ability to act as a gas barrier as in Example 3 were used. The gas-filled packaging was replaced with a vacuum packing. Variations in the amount of blood sampled were looked for in the same manner as in Example 3. The results are shown in Table 3.

The extent of the vacuum in the sample tube has changed, so that the amount or blood sampled has decreased compared to Example 3 and Example 4.

CONTROL 3

Vacuum blood-collection tubes were unwrapped and then studied in the same manner as for Example 3, using the same kinds of tubes as in that example. The results are shown in Table 3. The extent of vacuum in the tubes has markedly decreased, so that the amount of blood sampled has also markedly decreased compared to Examples 3 and 4.

TABLE 3

| | Blood sample before heating (ml) | Day 50 at 60° C. | Day 100 at 60° C. |
|---|---|---|---|
| Example 3 | 10.0 | 9.7 | 9.3 |
| Example 4 | 10.0 | 9.5 | 9.1 |
| Control 2 | 10.0 | 9.1 | 8.1 |
| Control 3 | 10.0 | 8.4 | 6.9 |

EFFECTS OF THE INVENTION

This invention, as mentioned above, provides a vacuum blood-collection tube in which whole-blood samples that have been collected coagulate in a short period of time, and that are centrifuged, resulting in an effective separation of the serum and the blood clot. In this kind of vacuum blood-collection tube, serum can be stored after the step of centrifugation, and the serum obtained can be stored for long periods of time at low temperatures.

The space between the vacuum blood-collection tube and the wrapping used to wrap the tube is filled with a gas that does not readily permeate either of these tube and wrapping materials and that is at a pressure greater than atmospheric pressure. Because of this gas filling, the low-pressure conditions of the inside of the tube-shaped vessel can be maintained with certainty over a long period of time. The ability of this wrapping to act as a gas barrier is much better than that of the wrapping used on conventional vacuum wrappings. The flexibility, lightness, and non-bulkiness of this wrapping is excellent, and it does not damage the vacuum tube. It is inexpensive, as well.

Figure 2:
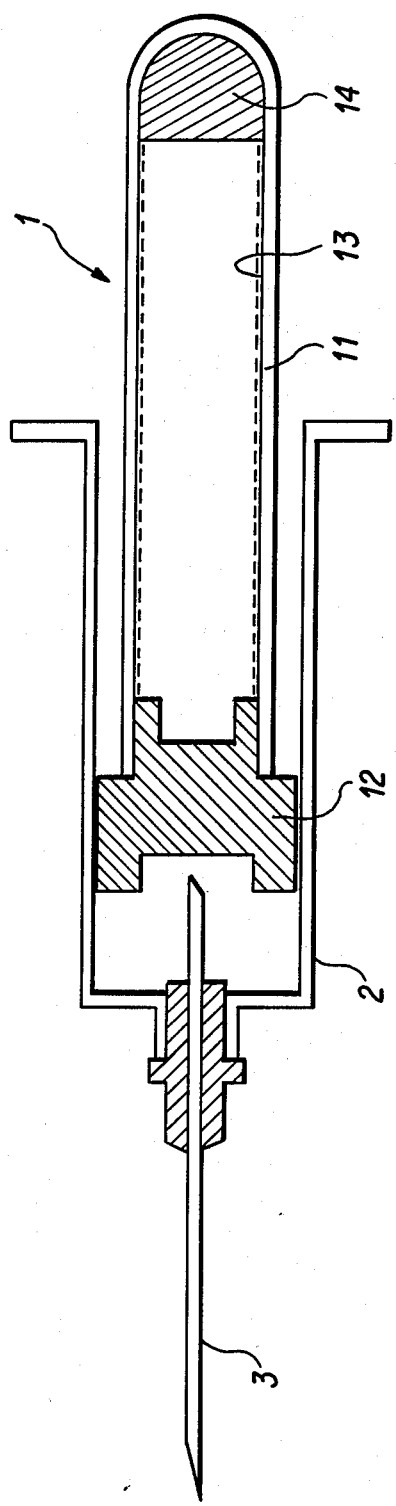
FIG. 2 illustrates a vacuum blood-collection tube of the present invention and the tube holder.

A vacuum blood-collection tube according to the present invention is illustrated in FIG. 2. The vacuum blood-collection tube 1 includes a tube-shaped vessel 11, a plug 12 which provides an air-tight opening in the vessel, blood coagulation accelerant 13 incorporated on the inner wall of the vessel, and serum-separator 14. Also illustrated in FIG. 2 is the tube holder 2 and cannula 3.

It is understood that various other modifications will be apparent to and can be readily made by those skilled in the art without departing from the scope and spirit of this invention. Accordingly, it is not intended that the scope of the claims appended hereto be limited to the description as set forth herein, but rather that the clams be construed as encompassing all the features of patentable novelty which reside in the present invention, including all features which would be treated as equivalents thereof by those skilled in the art to which this invention pertains.

What is claimed is:

1. A vacuum blood-collection tube comprising a tube-shaped vessel having an opening through which air can be removed, and a plug that makes the opening air-tight to maintain low-pressure conditions inside the said vessel, the raw materials of the said vessel being polyethyleneterephthalate, a copolymer of polyethyleneterephthalate, or an acrylonitrile resin, and the inner walls of said vessel incorporating a hydrophilic substance that is either difficult or impossible to dissolve in water and that prevents blood clots from adhering to the inner walls of said tube, a water-soluble substance, and an adsorptive inorganic substance.

2. A vacuum blood-collection tube according to claim 1, wherein said adsorptive inorganic substance has an absorption amount of linseed oil or 20–40 ml/100 g and a BET-specific surface area of 5,000–30,000 $cm^2/g$.

3. A vacuum blood-collection tube according to claim 1, wherein a partitioning agent is used within said vessel.

4. A vacuum blood-collection tube according to claim 3, wherein said partitioning agent contains both agents that confer the property of thixotropy and viscous liquid.

5. A vacuum blood-collection tube according to claim 3, wherein said partitioning agent contains thixotropy-conferring agents, viscous liquids and water-insoluble amines.

6. A vacuum blood-collecting tube according to any one of claims 1–5, wherein said tube-shaped vessel is wrapped so as to be air-tight in a plastic wrapping that acts as a gas barrier, the space between said tube-shaped vessel and said wrapping being filled with a gas that does not readily permeate either the vessel material or the wrapping material, and the pressure of said gas being greater than atmospheric pressure.

7. A vacuum blood-collection tube according to claim 6, wherein the amount of said gas that permeates both the tube-shaped vessel and the wrapping is 2 $cc/m^2 \cdot 24$ hrs atm or less at 23° C.

8. A vacuum blood-collection tube according to claim 7, wherein said wrapping is made of a laminate.

9. A vacuum blood-collection tube according to claim 1, wherein said hydrophilic substance that is either difficult or impossible to dissolve in water is a substance selected from the group consisting of dimethylpolysiloxane modified with polar substitutents, and methylhydrogenpolysiloxane modified with polar substituents.

10. A vacuum blood-clotting tube according to claim 9, wherein said adsorptive inorganic substance is selected from the group consisting of glass, silica, kaolin, cerite and benthonite.

11. A vacuum blood-clotting tube according to claim 10, wherein said water-soluble substance is selected from the group consisting of ethylene glycol, glycerin, sorbitol, polyethylene oxide, polyvinyl alcohol and polyvinyl pyrrolidone.

* * * * *